US012687533B2

(12) United States Patent
Schmitz

(10) Patent No.: US 12,687,533 B2
(45) Date of Patent: Jul. 21, 2026

(54) QUANTITATIVE ANALYSIS OF BIOMASS SAMPLES

(71) Applicant: Soliton, LLC, Sioux Falls, SD (US)

(72) Inventor: Tessanna Bauer Schmitz, Chancellor, SD (US)

(73) Assignee: Soliton, LLC, Sioux Falls, SD (US)

( * ) Notice: Subject to any disclaimer, the term of this patent is extended or adjusted under 35 U.S.C. 154(b) by 658 days.

(21) Appl. No.: 18/115,975

(22) Filed: Mar. 1, 2023

(65) Prior Publication Data

US 2026/0098846 A1 Apr. 9, 2026

Related U.S. Application Data

(60) Provisional application No. 63/316,175, filed on Mar. 3, 2022.

(51) Int. Cl.
*G01N 33/02* (2006.01)
*G01N 1/40* (2006.01)

(52) U.S. Cl.
CPC ......... *G01N 33/025* (2013.01); *G01N 1/4077* (2013.01)

(58) Field of Classification Search
CPC ...... G01N 33/025; G01N 1/4077; G01N 1/44; Y10T 436/143333; Y10T 436/18; Y10T 436/25
USPC .............................. 436/20, 94, 119, 155, 174
See application file for complete search history.

(56) References Cited

U.S. PATENT DOCUMENTS

| | | | |
|---|---|---|---|
| 4,525,218 | A | 6/1985 | Chen et al. |
| 8,399,224 | B2 | 3/2013 | Konieczny-Janda et al. |
| 8,518,467 | B2 | 8/2013 | Srinivasan et al. |
| 8,679,793 | B2 | 3/2014 | Lewis |
| 9,200,302 | B2 | 12/2015 | Comettini et al. |
| 9,335,043 | B2 | 5/2016 | Nguyen |
| 10,138,332 | B2 | 11/2018 | Jansen et al. |
| 2008/0057555 | A1* | 3/2008 | Nguyen .................... C12P 7/10 435/165 |
| 2010/0233771 | A1* | 9/2010 | McDonald ............. C12M 43/02 435/289.1 |
| 2013/0164795 | A1 | 6/2013 | Lowe et al. |
| 2013/0295629 | A1* | 11/2013 | Weider .................... C12P 19/02 435/157 |
| 2013/0309360 | A1 | 11/2013 | Lewis |
| 2015/0216203 | A1 | 8/2015 | Isaksen et al. |
| 2018/0363017 | A1 | 12/2018 | Tolan |
| 2022/0298532 | A1* | 9/2022 | Pal ............................ C12P 7/06 |

FOREIGN PATENT DOCUMENTS

| | | |
|---|---|---|
| WO | WO 2013/166469 A2 | 11/2013 |
| WO | WO 2014/202711 A1 | 12/2014 |
| WO | WO 2024/091515 A1 | 5/2024 |

OTHER PUBLICATIONS

Liu et al. Bioresource Technology, vol. 119, May 30, 2012, pp. 224-233.*

Amirkhani et al. Chemical Engineering Communications, vol. 202, 2015, pp. 1235-1244.*

Dunning et al., "Saccharification of Agricultural Residues" Jan. 1, 1945, Industrial & Engineering Chemistry, 37(1):6 pages.

International Patent Application No. PCT/US2023/035825, filed Oct. 24, 2023; International Preliminary Report on Patentability, mailed Sep. 25, 2024, 39 pages.

International Patent Application No. PCT/US2023/035825, filed Oct. 24, 2023; International Search Report / Written Opinion issued Feb. 15, 2024; 12 pages.

International Patent Application No. PCT/US2023/035825, filed Mar. 1, 2023; International Search Report / Written Opinion issued Feb. 15, 2024; 15 pages.

Adeogun, et al., "ZnCl₂ Enhanced Acid Hydrolysis of Pretreated Corncob for Glucose Production: Kinetics, Thermodynamics and Optimization Analysis", 2018, *Journal of Bioresources and Bioproducts*, 4(3):149-158.

Adney, "Measure of Cellulase Activities", Laboratory Analytical Procedure (LAP), Technical Report NREL/TP-510-42628, Issue Date Aug. 12, 1996, edition date Jan. 2008, National Renewable Energy Laboratory (NREL), Golden, Colorado, operated for the U.S. Department of Energy, 11 pages.

AOAC Official Method 930.15 Loss on Drying (Moisture) For Feeds.

AOAC Official Method 935.29 Moisture in Malt.

AOAC Official Method 942.05 Ash of Animal Feed.

AOAC Official Method 945.16 Oil in Cereal Adjuncts Petroleum Ether Extraction Method.

AOAC Official Method 990.03 Protein (Crude) In Animal Feed.

AOAC Official Method 995.16, "β-Glucan in Barley and Oats: Streamlined Enzymatic Method", First Action 1995, AOAC International, Rockville, Maryland, © 2000, 3 pages.

(Continued)

*Primary Examiner* — Maureen Wallenhorst

(74) *Attorney, Agent, or Firm* — Mueting Raasch Group

(57) ABSTRACT

A method for quantifying a cellulosic component in a sample includes hydrolyzing the sample in a single acid hydrolysis step of the sample in aqueous sulfuric acid having a concentration of 15 wt-% to 60 wt-%, at an incubation temperature of 50° C. to 98° C., at ambient pressure, for an incubation period of 30 min to 360 min; separating a supernatant from the hydrolyzed sample in aqueous sulfuric acid; analyzing the supernatant for total content of glucose and xylose and one or more of mannose, galactose, and arabinose; and calculating, based on the analysis, the amount of the cellulosic component, wherein the cellulosic component includes hemicellulose, cellulose, or both.

19 Claims, 5 Drawing Sheets

(56)             References Cited

OTHER PUBLICATIONS

AOAC Official Method 996.11 Starch (Total) in Cereal Products.

ASTM D1696-95 (Reapproved 2019), "Standard Test Method for Solubility of Cellulose in Sodium Hydroxide", Dec. 2019, ASTM International, West Conshohocken, Pennsylvania, 4 pages.

ASTM E3181-20, "Standard Practice for Determination of the Converted Fraction of Starch and Cellulosic Content From a Fuel Ethanol Production Facility", Mar. 2020, ASTM International, West Conshohocken, Pennsylvania, 10 pages.

Cao, et al., "Acid Hydrolysis of Cellulose in Zinc Chloride Solution", 1995, *Applied Biochemistry and Biotechnology*, 51/52:21-28.

Céspedes et al. "Quantification of digestive utilization of dietary fiber from corn co-products in grown pigs", 2015, Dissertation, Iowa State University, Ames, Iowa, 166 pages. Available online at core.ac.uk/download/pdf/38937737.pdf. Obtained from the internet on Sep. 2, 2023.

"Conversion of Corn-Kernel Fiber in Conventional Fuel-Ethanol Plants", Project No. 0340-19-03 (short version), Nov. 11, 2018, National Corn to Ethanol Research Center (NCERC), Edwardsville, Illinois, 7 pages.

Dahnum et al., "Comparison of SHF and SSF processes using enzyme and dry yeast for optimization of bioethanol production from empty fruit bunch", 2015, *Energy Procedia*, 68:107-116.

Federal Register, "Part III: Environmental Protection Agency: 40 CFR 40 Part 80, Regulation of Fuels and Fuel Additives: RFS Pathways II, and Technical Amendments to the RFS Standards and E15 Misfueling Mitigation Requirements; Final Rule", Jul. 18, 2014, vol. 79, No. 138, 42128-42167.

Flodman, et al., "Extraction of Soluble Fiber from Distillers' Grains", Dec. 2011, *Applied Biochemistry and Biotechnology*, 166(4):1070-81.

Gao et al., "Fast Hemicellulose Quantification Via a Simple One-Step Acid Hydrolysis", Jun. 2014, *Biotechnology and Bioengineering*, 111(6):1088-1096.

Gibson, "Fiber Frustration", May 10, 2021, Ethanol Producer Magazine, 3 pages. Available online at ethanolproducer.com/articles/18193/fiber-frustration. Obtained from the internet on May 18, 2021.

Iberahim et al., "Sodium Hydroxide Pretreatment and Enzymatic Hydrolysis of Oil Palm Mesocarp Fiber", Jun. 2013, *Int'l J Chem Eng and Appl*,4(3):101-105.

Janga et al., "Influence of Acid Concentration, Temperature, and Time on Decrystallization in Two-Stage Concentrated Sulfuric Acid Hydrolysis of Pinewood and Aspenwood: A Statistical Approach", 2012, *BioResources*, 7(1):391-411.

Kanchanalai et al., "Reaction Kinetics of Concentrated-Acid Hydrolysis for Cellulose and Hemicellulose and Effect of Crystallinity", 2016, *BioResources*, 11:1672-1689.

Kaur et al., "Efficient process engineering for extraction of hemicellulose from corn fiber and its characterization", 2020, *Carbohydrate Polymer Technology and Applications*, 1:100011, 7 pages. Available online Oct. 13, 2020.

Kukielski et al., "Maximize Ethanol Production from Corn Starch, Resistant Starch, Cellulose and Xylan", NCERC at Southern Illinois University, Edwardsville, Illinois, 14 pages. No date available. Believed to be available as early as Aug. 5, 2021. Available online at fs.hubspotusercontent00.net/hubfs/8341404/FELC%202021%20Yan%20Zhang%20Corn%20Kernel%20Fiber.pdf.

Li et al., "In-situ corn fiber conversion improves ethanol yield in corn drymill process", Mar. 2018, *Industrial Crops and Products*, 113:217-224.

Mandels et al., "Enzymatic Hydrolysis of Waste Cellulose", 1974, *Biotechnology and Bioengineering*, vol. XVI, John Wiley & Sons, Inc. pp. 1471-1493.

Marlett, et al., "Comparison of In Vitro and In Vivo Measures of Resistant Starch in Selected Grain Products", 1996, *Cereal Chemistry*, 73(1):63-68. Available online at cerealsgrains.org/publications/cc/backissues/1996/Documents/73_63.pdf. Obtained from the internet on Sep. 2, 2023.

Megazyme, "Mushroom and Yeast Beta-Glucan Assay Procedure", 2021, Megazyme, Bray, Ireland, 16 pages.

Memorandum to Air and Radiation Docket EPA-HQ-OAR-2012-0401, "Additional Detail on the Calculation of the Cellulosic Converted Fraction, and Attribution of Batch RINs for D-code Dependent Feedstocks", Jul. 1, 2014, U.S. Environmental Protection Agency (EPA), Washington, DC, 11 pages.

Michel et al., "Determination of Cellulosic Glucan Content in Starch Containing Feedstocks," Laboratory Analytical Procedure (LAP), Technical Report NREL/TP-2800-76724, Issue Date Feb. 2021, National Renewable Energy Laboratory (NREL), Alliance for Sustainable Energy, LLC, Golden, Colorado, operated for the U.S. Department of Energy, 20 pages.

Moxley, Thesis, "Studies of Cellulosic Ethanol Production from Lignocellulose", Jun. 8, 2007, Virginia Polytechnic Institute and State University, Blacksburg, Virginia, 82 pages.

Moxley, et al., "More Accurate Determination of Acid-Labile Carbohydrates in Lignocellulose by Modified Quantitative Saccharification", 2007, *Energy & Fuels*, 21:3684-3688. Available online Oct. 18, 2007.

Searle, "A seemingly innocuous cellulosic biofuel pathway", May 28, 2019, International Council on Clean Transportation, 5 pages. Available online at theicct.org/blog/staff/seemingly-innocuous-cellulosic-biofuel-pathway. Obtained from the internet on Apr. 9, 2021.

Sluiter et al., "Compositional Analysis of Lignocellulosic Feedstocks. 1. Review and Description of Methods", 2010, *J Agric Food Chem* 58(16):9043-9053. Published online Jul. 29, 2010.

Sluiter et al., "Determination of Sugars, Byproducts, and Degradation Products in Liquid Fraction Process Samples", Laboratory Analytical Procedure (LAP), Technical Report NREL/TP-510-42623, Issue Date Dec. 8, 2006, edition date Jan. 2008, National Renewable Energy Laboratory (NREL), Golden, Colorado, operated for the U.S. Department of Energy, 14 pages.

Sluiter et al., "Determination of Structural Carbohydrates and Lignin in Biomass", Laboratory Analytical Procedure (LAP), Technical Report NREL-TP-510-42618, Issue Date Apr. 2008, Revision Date Aug. 3, 2012, National Renewable Energy Laboratory (NREL), Alliance for Sustainable Energy, LLC, Golden, Colorado, operated for the U.S. Department of Energy, 18 pages.

Sluiter et al., "Direct determination of cellulosic glucan content in starch containing samples", Jan. 15, 2021, *Cellulose*, 14 pages. Available online at doi-org/10.1007/s10570-020-03652-2.

Sluiter, et al., "Summative Mass Closure", Laboratory Analytical Procedure (LAP) Review and Integration, Technical Report NREL/TP-510-48087, Issue Date Apr. 2010, Revision Date Jul. 8, 2011, National Renewable Energy Laboratory (NREL), Alliance for Sustainable Energy, LLC, Golden, Colorado, operated for the U.S. Department of Energy, 13 pages.

Topic, "Hemicellulose", 2020, *Science Direct*, 12 pages.

Topic, "Xylanases", 2014, *Science Direct*, 10 pages.

Van Soest et al., "Symposium: Carbohydrate Methodology, Metabolism, and Nutritional Implications in Dairy Cattle: Methods for Dietary Fiber, Neutral Detergent Fiber, and Nonstarch Polysaccharides in Relation to Animal Nutrition", 1991, *J Dairy Sci*, 74:3583-3597.

Wang et al., "Comparative Study of Alkali and Acidic Cellulose Solvent Pretreatment of Corn Stover for Fermentable Sugar Production", 2016, *BioResources*, 11(1):482-491.

Wang, "Experiment No. 4, Cellulose Degradation", Department of Chemical & Biomolecular Engineering course ENCH485, University of Maryland, College Park, Maryland, 6 pages. No publication date available, believed to be available as early as 2009. Obtained from the internet May 5, 2021.

Wu et al., "Effect of $H_2O_2$ Bleaching Treatment on the Properties of Finished Transparent Wood", May 1, 2019, *Polymers* 11:773, 13 pages.

Wyman et al., "*Hydrolysis of Cellulose and Hemicellulose*" in Polysaccharides: Structural Diversity and Functional Versatility 995 (Several Dumitriu ed., 2004). 167 pages plus cover page. Available online Aug. 13, 2015.

\* cited by examiner

QUANTITATIVE ANALYSIS OF BIOMASS SAMPLES

This application claims priority to U.S. Provisional Patent Application Ser. No. 63/316,175, filed Mar. 3, 2022, the disclosure of which is incorporated herein by reference.

FIELD

The present disclosure relates to methods for compositional analysis of cellulosic feedstocks. The present disclosure further relates to methods for compositional analysis of corn kernel fiber and other similar materials.

BACKGROUND

Lignocellulosic biomass is a complex material that is made up of three main structural polymers: cellulose, hemicellulose, and lignin. Cellulose is a linear polysaccharide containing linked β-1,4-gluclose units. The glucose units are linked to one another by hydrogen bonds and can form a crystalline or amorphous structure. Hemicellulose is a heteropolymer containing xylan, mannan, and glucans in different amounts depending on the source. Hemicelluloses are amorphous and include branched chains that are shorter than the chains in cellulose (about 500 to 3000 sugar units compared to 7000 to 15000 sugar units in cellulose). Xylans are primarily made up of xylose residues but may also be substituted with other sugars, such as glucose and arabinose. Mannans include two types, galactomannans made up of mannopyranose, and glucomannans made up of mannopyranose and glucopyranose. Glucans include mixed linkage β-glucans and xyloglucans, made up of glucose residues or glucose and xylose residues, respectively.

Cellulosic feedstocks can be broken down to their components and used to manufacture various chemicals, such as fuel ethanol. The term "conversion" is often used in the industry to refer to a material's conversion to ethanol. Thus, "cellulosic conversion" typically refers to cellulose or cellulosic material converted to ethanol, and "starch conversion" refers to the conversion of starch to ethanol. In order for manufacturers of cellulosic ethanol to access financial incentives offered by the government, the Environmental Protection Agency ("EPA") Renewable Fuel Standard ("RFS") requires analytical verification that the carbohydrates converted to ethanol originate from non-starch (i.e., cellulosic) material.

SUMMARY

A method for quantifying a cellulosic component in a sample includes preparing a suspension by mixing an amount of sample with aqueous sulfuric acid having a concentration of 15 wt-% to 60 wt-%; incubating the suspension at an incubation temperature of 50° C. to 98° C. at ambient pressure for an incubation period of 30 min to 360 min, wherein the sample is not subjected to hydrolysis at temperatures above 98° C.; separating a supernatant from the suspension; analyzing the supernatant for total content of glucose and xylose and one or more of mannose, galactose, and arabinose; and calculating, based on the analysis, the amount of the cellulosic component, wherein the cellulosic component includes hemicellulose, cellulose, or both.

A method for quantifying a cellulosic component in a sample includes hydrolyzing the sample in a single acid hydrolysis step of the sample in aqueous sulfuric acid having a concentration of 15 wt-% to 60 wt-%, at an incubation temperature of 50° C. to 98° C., at ambient pressure, for an incubation period of 30 min to 360 min; separating a supernatant from the hydrolyzed sample in aqueous sulfuric acid; analyzing the supernatant for total content of glucose and xylose and one or more of mannose, galactose, and arabinose; and calculating, based on the analysis, the amount of the cellulosic component, wherein the cellulosic component includes hemicellulose, cellulose, or both.

The sample may be corn-based. The sample may include corn kernel fiber. The sample may include a starting material, an intermediate product, or a final product from a corn-to-ethanol production process.

The amount of sample mixed with an amount of the aqueous sulfuric acid may be from 8 to 12 parts of aqueous sulfuric acid to every 1 part sample. The sample may not be subjected to hydrolysis at temperatures above 90° C. The sample may be only subjected to temperatures or 90° C. or lower during the method. The supernatant may be substantially free of furfural and hydroxymethylfurfural.

The method may include calculating hemicellulose as:

$$\% \ dw \ \text{Total Hemicellulose} = \left( \frac{\left( \frac{X-Y+S-T}{100} \right) * (A+R)}{A} \right) \bigg/ \left( 1.136 * \left( \frac{D}{100} \right) \right) * 100,$$

where:
R is a total weight of liquid added to the sample;
A is mass of the sample;
D is wt-% total solids content of the sample;
S is the arabinose content of the sample in wt-%;
T is an HPLC result representative of arabinose of a blank sample in wt-%;
X is a combined xylose, galactose, and mannose content of the sample in wt-%; and
Y is an HPLC result representative of combined xylose, galactose, and mannose of the blank sample in wt-%.

The method may further include quantifying the starch concentration of the sample and calculating the cellulose concentration using the starch concentration.

An analysis result including a hemicellulose concentration of a sample may be obtained by: preparing a suspension by mixing an amount of sample with aqueous sulfuric acid having a concentration of 15 wt-% to 60 wt-%; incubating the suspension at an incubation temperature of 50° C. to 98° C. at ambient pressure for an incubation period of 30 min to 360 min, wherein the sample is not subjected to hydrolysis at temperatures above 98° C.; separating a supernatant from the suspension; analyzing the supernatant for total content of glucose and xylose and one or more of mannose, galactose, and arabinose; and calculating, based on the analysis, the amount of the hemicellulose in the sample.

DEFINITIONS

Figure 1A:
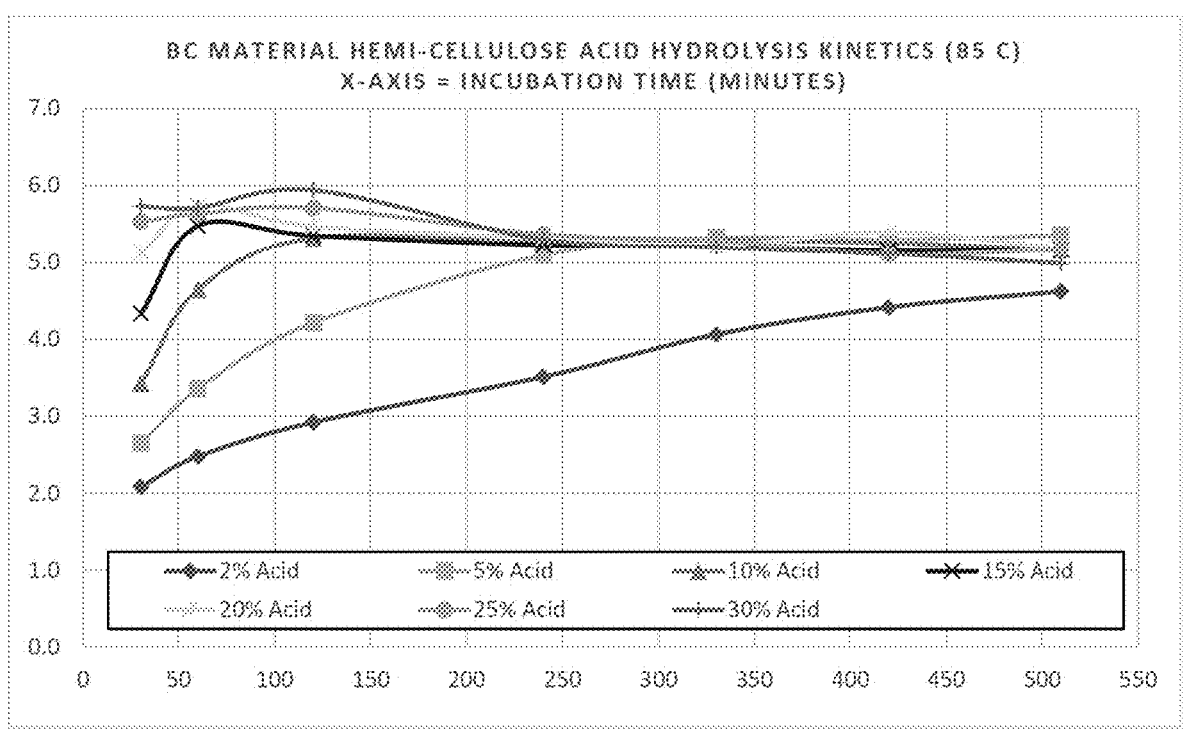
FIG. 1A is a graphical representation of the impact of acid concentration and incubation time on the hydrolysis of hemicellulose in pre-conversion material as described in EXAMPLE 1.
Figure 1B:
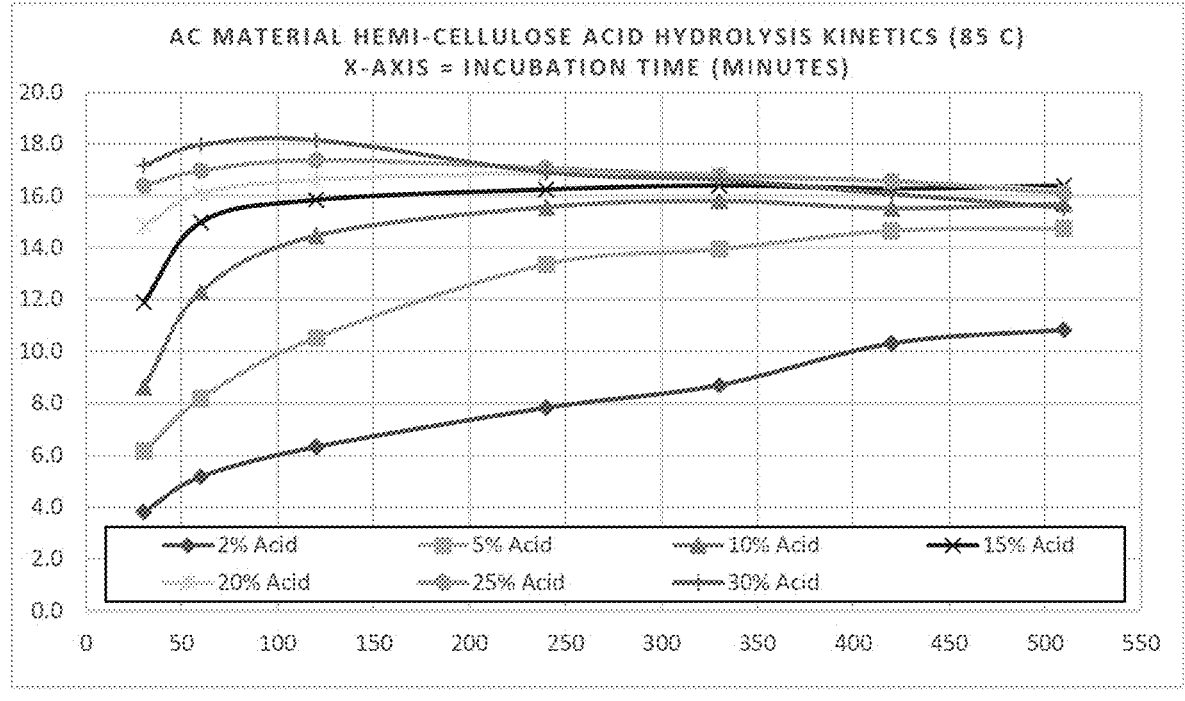
FIG. 1B is a graphical representation of the impact of acid concentration and incubation time on the hydrolysis of hemicellulose in post-conversion material as described in EXAMPLE 1.
Figure 1C:
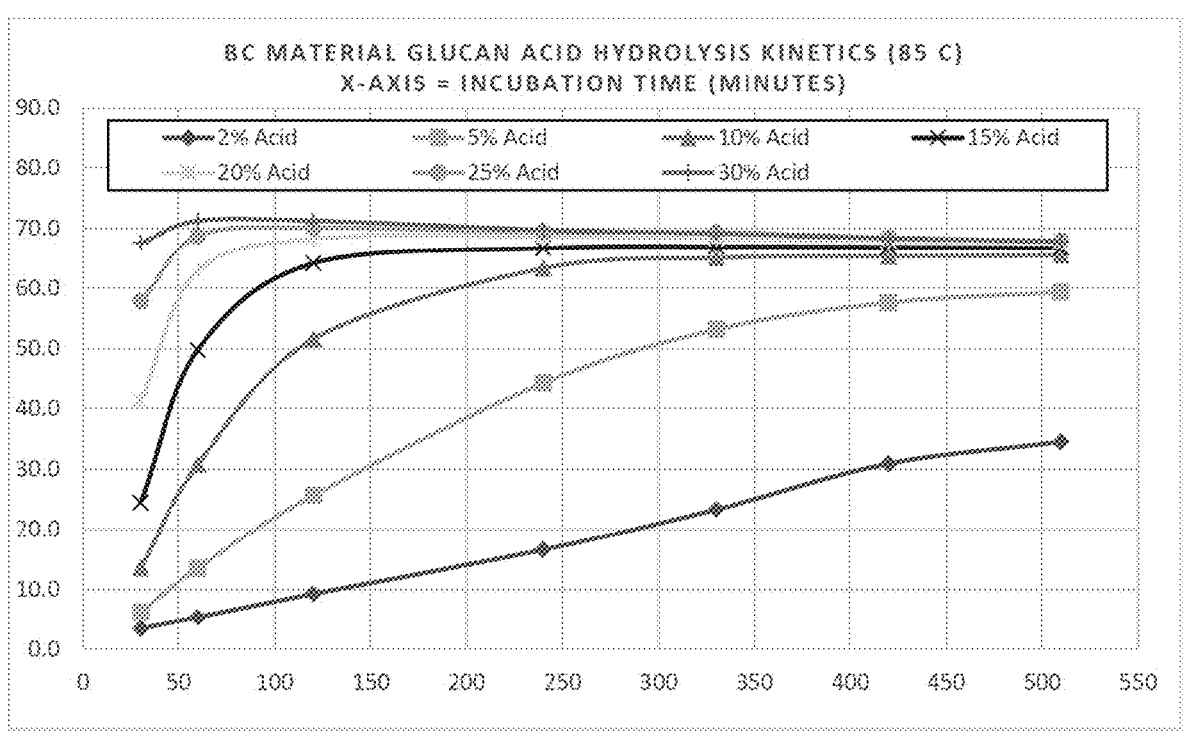
FIG. 1C is a graphical representation of the impact of acid concentration and incubation time on the hydrolysis of glucan in pre-conversion material as described in EXAMPLE 1.
Figure 1D:
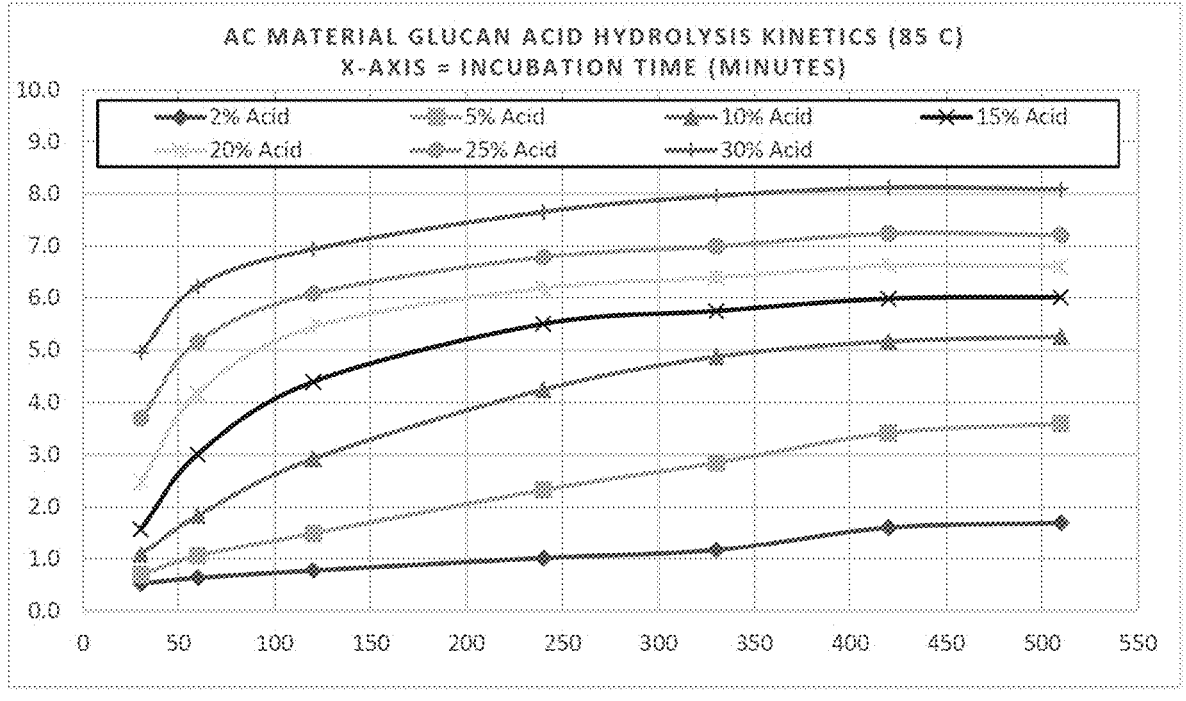
FIG. 1D is a graphical representation of the impact of acid concentration and incubation time on the hydrolysis of glucan in post-conversion material as described in EXAMPLE 1.
Figure 1E:
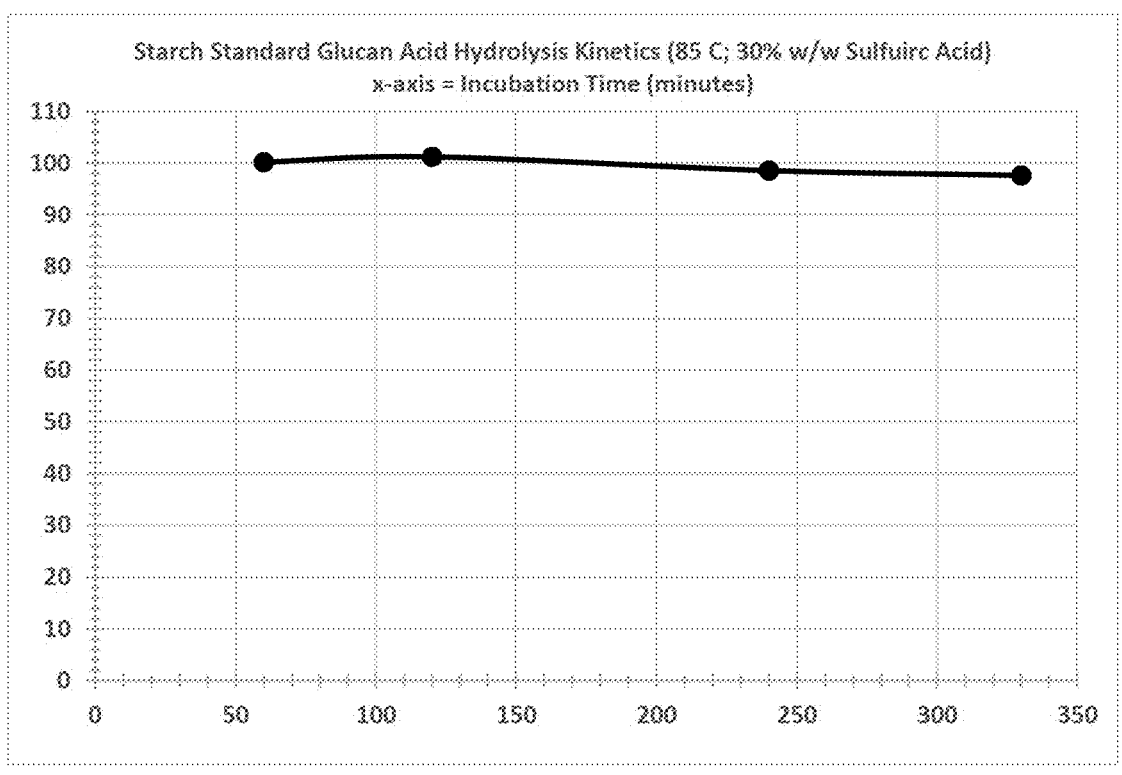
FIG. 1E is a graphical representation of the impact of incubation time on the hydrolysis of a starch standard as described in EXAMPLE 1.
Figure 1F:
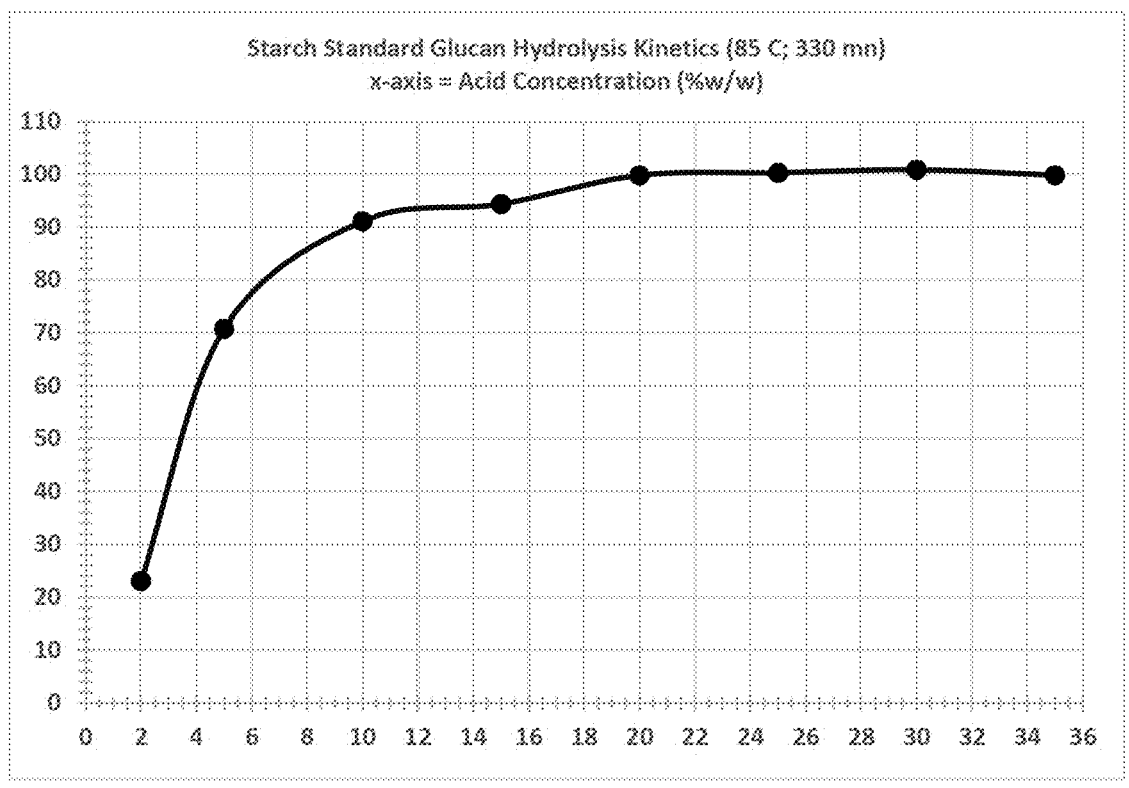
FIG. 1F is a graphical representation of the impact of acid concentration on the hydrolysis of a starch standard as described in EXAMPLE 1.

All scientific and technical terms used herein have meanings commonly used in the art unless otherwise specified. The definitions provided herein are to facilitate understanding of certain terms used frequently herein and are not meant to limit the scope of the present disclosure.

The term "cellulosic content" is used here to refer to the combination of cellulose, hemicellulose, and lignin.

The term "cellulosic components" is used here to refer to cellulose and hemicellulose. "A cellulosic component" is intended to mean either cellulose or hemicellulose, individually.

The term "cellulosic materials" is used here to refer to materials that contain cellulosic components.

The term "fiber" is commonly used in the industry to refer to both the fiber fraction of grains, such as corn, as well as an analytical parameter. Here, the fiber fraction of corn is referred to as "corn kernel fiber" and the analytical parameter is referred to as "fiber."

The term "substantially" as used here has the same meaning as "significantly," and can be understood to modify the term that follows by at least about 90%, at least about 95%, or at least about 98%.

The term "substantially free" is used here to mean that the compound in question is present in the composition at a level of 1 wt-% or lower, including 0 wt-%.

The term "not substantially" as used here has the same meaning as "not significantly," and can be understood to have the inverse meaning of "substantially," i.e., modifying the term that follows by not more than 25%, not more than 10%, not more than 5%, or not more than 2%.

The term "about" is used here in conjunction with numeric values to include normal variations in measurements as expected by persons skilled in the art, and is understood to have the same meaning as "approximately" and to cover a typical margin of error, such as +5% of the stated value.

Terms such as "a," "an," and "the" are not intended to refer to only a singular entity, but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination of any two or more of the listed elements.

The recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" or "at least" a particular value, that value is included within the range.

As used here, "have," "having," "include," "including," "comprise," "comprising," or the like are used in their open-ended sense, and generally mean "including, but not limited to." It will be understood that "consisting essentially of," "consisting of," and the like are subsumed in "comprising" and the like. As used herein, "consisting essentially of," as it relates to a composition, product, method, or the like, means that the components of the composition, product, method, or the like are limited to the enumerated components and any other components that do not materially affect the basic and novel characteristic(s) of the composition, product, method, or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Any direction referred to here, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

DETAILED DESCRIPTION

The present disclosure relates to methods for compositional analysis of cellulosic feedstocks. The present disclosure further relates to methods for compositional analysis of corn kernel fiber and other similar materials.

Quantitation of cellulose, hemicellulose, fiber, and lignin in lignocellulosic materials is desired, for example, because in order to claim government benefits available to producers of renewable cellulosic fuels (e.g., ethanol), the producers must differentiate between starch-based fuels and fuels derived from cellulosic components. Many producers use an in-situ cellulosic conversion, where cellulosic sugars become mixed with starch-based sugars prior to conversion to ethanol. Other producers use fractionated corn kernel fiber or post-conversion materials (e.g., after conversion of starch to ethanol) as their feedstock in the cellulosic conversion process. Post-conversion materials from corn-to-ethanol fermentation typically contain corn kernel fiber, germ, and other residual materials. Depending on the efficiency of the conversion process, the post-conversion material may also contain some starch. The starch-based fuels and fuels derived from cellulosic components can be differentiated by analyzing the feedstock used in the fuel production and reporting the relative amounts of starch and cellulosic components converted to fuel.

The EPA identifies ethanol produced from cellulosic materials by a renewable identification number ("RIN") D3. Thus, the relative amount of ethanol produced from cellulosic content versus starch is sometimes referred to as "% D3

RIN." The California Air Resources Board ("CARB") has also implemented a Low Carbon Fuel Standard ("LCFS") that requires fuels supplied for use in California to meet certain carbon intensity standards. Cellulosic ethanol qualifies as a Low Carbon Intensity ("CI") Fuel under the CARB LCFS.

Quantitation of cellulose, hemicellulose, fiber, and lignin in lignocellulosic materials is challenging due to the varied chemical structures within the materials and the compounds of interest, the lack of analytical methods to directly measure the compounds of interest, and the difficulty in breaking down the compounds into measurable components without causing degradation or unintended chemical reactions.

Methods for determining carbohydrate composition in lignocellulosic materials typically include various steps that attempt to quantitatively saccharify the various compounds within the material to quantifiable components, such as simple sugars. The National Renewable Energy Laboratory ("NREL") has developed various test methods over the years (including versions released 1996, 2006, and 2021) that are widely used in the renewable fuels industry. Typical compositional methods for biomass analysis involve a primary hydrolysis in strong (e.g., 72 wt-%) sulfuric acid at a low temperature (ambient to 30° C.) to convert polysaccharides into oligosaccharides, and a secondary hydrolysis in weak (e.g., 3 wt-% to 4 wt-%) sulfuric acid at a high temperature (e.g., boiling to 125° C.) and optionally at high pressure to convert the oligosaccharides to monosaccharides. The handling of samples in concentrated sulfuric acid and of boiling sulfuric acid under pressure cause the need for additional laboratory safety measures and specialized equipment.

Further challenges in cellulosic glucan quantification in samples that contain starch or free sugars derived from starch are caused by the fact that starch and cellulose are both glucan-based polymers and differ chemically only by a single bond orientation. A standard cellulose determination method issued by AOAC International in 2012 involves acid hydrolysis of glucan polymers to glucose, followed by glucose measurement by HPLC. However, glucose derived from starch is identical to glucose derived from cellulose, and the source of the glucose after acid hydrolysis cannot be determined.

In conventional methods, to quantify the amount of cellulose in a sample, the sample is tested twice to separately determine the total amount of glucose derived by acid hydrolysis, and the amount of glucose derived from starch by enzymatic hydrolysis. To quantify hemicellulose in addition to cellulose, the amounts of other sugars, including xylose, mannose, galactose, and arabinose, are also determined. The amount of cellulose is then calculated by subtracting the starch-based glucose from the total glucose. Accurate cellulose quantification, therefore, relies on the ability to accurately quantify both cellulose and starch. One issue experienced with this approach is that starch includes both labile and resistant starch moieties. During conventional cellulose acid hydrolysis, due to the different reactivities of the starch and cellulose to acid hydrolysis, there is likely a significant bias in the calculated cellulose content when substantial amounts of starch or free sugars are present. Further, the analytical methods currently used to quantify cellulose and hemicellulose are complex and difficult to perform and may require specialized equipment.

Some researchers have suggested adding another method step to remove starch-based glucans or adding a parallel control to account for degradation of sugars during analysis. See, e.g., Moxley and Zhang, *More Accurate Determination*

*of Acid-Labile Carbohydrates in Lignocellulose by Modified Quantitative Saccharification*, 21 Energy and Fuels 3684 (2007), suggesting a parallel secondary hydrolysis, and Sluiter et al., *Direct determination of cellulosic glucan content in starch-containing samples*, Cellulose (2021), suggesting an enzymatic hydrolysis step to hydrolyze and remove starch-derived glucose prior to acid hydrolysis. Moxley and Zhang also point out that different sugars degrade at different rates in the acid hydrolysis conditions.

The existing methods and added improvements still result in complicated analytical methods. The commonly used acid hydrolysis with concentrated sulfuric acid presents safety concerns and causes a need for additional precautions at laboratories. The acid hydrolysis performed with weaker acid but at high temperature and pressure requires specialized equipment, adding to the cost of analysis.

It would be desirable to provide an analytical method that can be performed in fewer steps than methods currently used in the industry. It would be desirable to provide an analytical method that can be performed without specialized equipment. It would further be desirable to provide an analytical method that is capable of quantifying starch, cellulose, and/or hemicellulose. It would be desirable to provide an analytical method that does not result in sugar degradation during the method. It would further be desirable to provide an analytical method that can provide a total cellulosic components (combined cellulose and hemicellulose), sometimes referred to as total fiber content, of cellulosic materials.

According to an embodiment, a method for compositional analysis of cellulosic materials is provided. The method includes a single hydrolysis step that can be performed at ambient pressure and below the boiling point of water. The method may be performed without specialized equipment. The method may be used to quantify hemicellulose in cellulosic materials, particularly in corn-based cellulosic materials, such as raw ground corn and starting materials and residual materials from corn-to-ethanol processes. The method may be used to quantify glucan and hemicellulose in cellulosic materials, particularly in corn-based cellulosic materials, such as raw ground corn and starting materials and residual materials from corn-to-ethanol processes. The method may be used to quantify total glucan and to calculate the amount of cellulose based on the total glucan and starch. The method does not cause any significant degradation of sugars during the method. The method may be used to provide a total cellulosic components (combined cellulose and hemicellulose), sometimes referred to as total fiber content, of cellulosic materials. The method may be combined with other proximate analyses, such as protein, fat, starch, and ash, to provide a full mass closure of a sample.

The methods of the present disclosure are particularly useful for quantifying one or more cellulosic components, hemicellulose and/or cellulose, in com-based cellulosic materials. The cellulosic components of corn are primarily present in corn kernel fiber. One of the challenges presented in quantifying the amount of cellulose is caused by starch, which is often present in corn-based products at least in minor amounts even after processing (e.g., after fractionation and/or ethanol production). The hemicellulose in corn, however, is mostly made up of xylose, mannose, galactose, and arabinose residues and does not contain significant amounts of glucose residue. The methods of the present disclosure are particularly useful for quantifying hemicellulose in corn and corn-based products. In some preferred embodiments, the methods of the present disclosure include quantifying hemicellulose in raw ground corn or a corn-based starting material in a corn-to-ethanol process. In some preferred embodiments, the methods of the present disclosure include quantifying hemicellulose in raw ground corn.

According to an embodiment, the method utilizes a diluted acid concentration (below 40 wt-%) and a low temperature (below the boiling point of water) at ambient pressure in a single hydrolysis step in order to break down the cellulosic material while avoiding degradation of the sugars. Ambient pressure is intended to mean normal atmospheric pressure, although some minor pressure build-up may occur in capped test tubes when heated to the hydrolysis temperature. The method does not include, however, the use of a pressurized enclosure, such as a closed autoclave heated to 100° C. or higher. The method includes quantification of the starch content of the sample and the resulting monosaccharides from the acid hydrolysis, and the calculation of the amounts of cellulose or hemicellulose or both cellulose and hemicellulose present in the initial sample. In some embodiments, the method includes calculation of the amount of hemicellulose.

The sample may be a grain-based sample. Some non-limiting examples of grains include corn, sorghum, wheat, barley, and the like. While any types of grain-based samples may be analyzed using the method, the method may be particularly useful for analyzing grain-based samples in conjunction with renewable fuel production. In some embodiments, the sample is corn, a fraction of corn, or a residual of corn. In some embodiments, the sample contains corn kernel fiber. The sample may be primarily corn kernel fiber. The sample may be a starting material, an intermediate product, or a final product from an ethanol production process, such as a corn-to-ethanol production process (e.g., a dry grind ethanol process) or a sorghum-to-ethanol production process. An example of a starting material from a corn-to-ethanol production process is corn, corn flour, a corn fraction, or the like, mash, or slurry substrate. In some embodiments, the sample is or contains raw ground corn (e.g., corn flour). Raw ground corn is understood to mean corn that has been ground but not cooked or treated, e.g., enzymatically. An example of an intermediate product from a corn-to-ethanol production process is wet cake, which is a post-fermentation mixture of remaining solids and liquid. An example of a final product from a corn-to-ethanol production process is dried distiller's grains (optionally with solubles), DDG(S), which is a dried post-fermentation mixture of remaining solids, optionally mixed with soluble solids. Similar corresponding starting materials, intermediate products, and final products may be analyzed from a sorghum-to-ethanol process. The sample may also be any number of animal feed or human food products. In particular, the sample may be a grain-based feed or food product.

The samples may be prepared for analysis by drying, grinding, or both drying and grinding. Samples that have a moisture content of 10 wt-% or greater may dried, for example, in an oven or by another suitable dehydration process without increasing the sample temperature above 50° C. According to an embodiment, the sample has a moisture content of less than 10 wt-% prior to beginning the compositional analysis. Alternatively, the moisture content of the sample is as-is, even if the moisture content is higher than 10 wt-%. In such cases, the amount and concentration of acid is adjusted so that a desired acid concentration in the hydrolysis solution is reached.

Samples that cannot pass (at least 95 wt-%) through a 0.5 mm screen are ground by any suitable method such that at least 95 wt-% of the sample passes through a 0.5 mm screen, with the remainder passing through a 1 mm screen. According to an embodiment, at least 95 wt-% of the sample passes through a 0.5 mm screen, with the remainder passing through a 1 mm screen prior to beginning the compositional analysis.

The compositional analysis may be performed on any suitable sample size. For practical reasons, a sample size between 0.5 g and 5 g (e.g., 1.0 g±0.10 g) may be used. However, the method is not particularly limited by the sample size, and the amounts of other reagents may be adjusted according to the sample size used.

The method of the present disclosure includes a single acid hydrolysis step. During the acid hydrolysis, a sample is incubated in a hydrolysis solution containing an acid. The hydrolysis solution is an aqueous solution. The sample and the hydrolysis solution may be mixed to form a suspension. According to an embodiment, the acid is sulfuric acid. The acid is present in the hydrolysis solution at a concentration of 10 wt-% or greater, 15 wt-% or greater, 20 wt-% or greater, or 25 wt-% or greater. The acid may be present in the hydrolysis solution at a concentration of 60 wt-% or lower, 50 wt-% or lower, 45 wt-% or lower, 40 wt-% or lower, or 35 wt-% or lower. In some embodiments, the acid is present in the hydrolysis solution at a concentration of 10 wt-% to 60 wt-%, 15 wt-% to 45 wt-%, or 20 wt-% to 35 wt-%. In one exemplary embodiment, the acid concentration is 30 wt-%. The amount of aqueous acid (volume per weight) mixed with the sample may be about 10 parts acid to every 1 part sample, or from 8 to 12 parts acid to every 1 part sample. The exact amount of acid is not particularly consequential as long as it is sufficient to hydrolyze the sample. However, the amount of acid is recorded for calculation of the final results of the analysis.

The sample may be incubated in the hydrolysis solution at an incubation temperature of 50° C. or greater, 60° C. or greater, 70° C. or greater, 75° C. or greater, or 80° C. or greater. The incubation temperature may be 98° C. or lower, 95° C. or lower, 90° C. or lower, or 85° C. or lower. In some embodiments, the incubation temperature is from 50° C. to 98° C., 60° C. to 95° C., or from 70° C. to 90° C. In one exemplary embodiment, the incubation temperature is 85° C.

The sample may be incubated in the hydrolysis solution for the duration of an incubation period of 30 min or greater, 45 min or greater, or 60 min or greater. The incubation period may be 360 min (6 h) or less, 300 min or less, 240 min or less, 180 min or less, 150 min or less, or 120 min or less. In some embodiments, the incubation period is from 30 min to 360 min, 45 min to 240 min, or 60 min to 150 min. In one exemplary embodiment, the incubation period is 120 min. The samples may be mixed during the incubation period to ensure exposure of all the sample particles to acid. For example, the samples may be mixed periodically throughout the incubation period, such as every 30 min or 60 min.

According to an embodiment, the hydrolysis is performed at conditions that do not result in substantial degradation of the sugars. That is, the hydrolysis conditions do not result in substantial formation of degradation products, such as furfural and hydroxymethylfurfural ("HMF"). After incubation of the sample in the hydrolysis solution, the sample forms a composition that contains monomeric sugars but is substantially free of furfural and HMF.

After incubation of the sample in the hydrolysis solution, a supernatant may be separated from the suspension. Any suitable separation method may be used. For example, to separate the supernatant from any suspended solids, the sample may be centrifuged and filtered (e.g., using a 0.2 μm filter). The supernatant may be separated and analyzed for total content of glucose and xylose and one or more of mannose, galactose, and arabinose. In some embodiments, the supernatant is analyzed for glucose, xylose, mannose, galactose, and arabinose content using. for example, a chromatographic method, such as HPLC. Any suitable HPLC method may be used. One suitable HPLC column for sugar analysis is the AMINEX HPX-87H column available from Bio-Rad Laboratories, Inc. in Hercules, CA. The amounts of the sugars obtained by HPLC analysis may be adjusted using a weight gain factor. The weight gain on hydrolysis for pentoses (C5 sugars) is 1.136, and for hexoses (C6 sugars) it is 1.111. In methods where xylose, mannose, and galactose co-elute from the HPLC column, the 1.136× weight gain factor may be used for all of these sugars, although it may result in a slight underestimation of hemicellulose if mannose or galactose are present.

A blank may be run alongside with the samples during analysis to account for any errors during the procedure. A pure starch standard may also be run alongside the samples to verify good method recovery and confirm the absence of degradation of the monosaccharides.

The amount of hemicellulose in the sample may be calculated using the following formula (I):

$$\% \ dw \ \text{Total Hemicellulose} = \left( \frac{\left( \frac{X - Y + S - T}{100} \right) * (A + R)}{A} \right) \Big/ \left( 1.136 * \left( \frac{D}{100} \right) \right) * 100,$$

where:
A is the mass of the sample;
R is a total weight of liquid added to the sample;
S is the arabinose content of the sample in wt-%;
T is the HPLC result representative of arabinose of the blank sample in wt-%;
X is the combined xylose, galactose, and mannose content of the sample in wt-%;
Y is the HPLC result representative of combined xylose, galactose, and mannose of the blank sample in wt-%;
1.136 is the weight gain on hydrolysis;
D is the wt-% total solids content of prepared sample.

The cellulose content of the sample may be calculated in a similar manner from the glucan content of the sample in wt-%, subtracting the amount of starch (e.g., the amount of glucose derived from starch in the sample) from the glucan content. The amount of glucan in the sample may be calculated using the following formula (II):

$$\% \ dw \ \text{Total Glucan} = \left( \frac{\left( \frac{X - Y}{100} \right) * (A + R)}{A} \right) \Big/ \left( 1.111 * \left( \frac{D}{100} \right) \right) * 100,$$

where:
A is the mass of the sample;
R is a total weight of liquid added to the sample;
X is the glucose content of the sample in wt-%;
Y is the glucose content of the blank in wt-%;
1.111 is the weight gain on hydrolysis;
D is the wt-% total solids content of prepared sample.
The amount of cellulose may be calculated using the following formula (III):

$$\% \ dw \ \text{Cellulose} = \% \ dw \ \text{Total Glucan} - \% \ dw \ \text{Starch}.$$

According to an embodiment, the method does not include any other hydrolysis steps, such as an enzymatic hydrolysis. For example, the method does not include an enzymatic hydrolysis step before acid hydrolysis. The elimination of the enzymatic hydrolysis step prior to acid hydrolysis, combined with acid hydrolysis at mild conditions, is believed to yield more accurate results for total hemicellulose and total glucan. An enzymatic hydrolysis may be performed separately to determine the starch content of the sample.

According to an embodiment, the method accurately quantitates the cellulosic components of the sample. The method may be able to quantify cellulose with an accuracy of 90% or greater, 95% or greater, or 98% or greater. The method may be able to quantify hemicellulose with an accuracy of 90% or greater, 95% or greater, or 98% or greater.

To be able to appropriately calculate the hemicellulose or cellulose content of the sample, the moisture content of the prepare sample is analyzed using any suitable moisture analysis method. Examples of suitable moisture analysis methods include AOAC Official Method 930.15 Loss on Drying (Moisture) For Feeds, and AOAC Official Method 935.29 Moisture in Malt. Prior to hydrolysis, the sample may be split and a portion of the sample may be analyzed for starch content using a starch assay. One useful starch assay is the Association of Official Analytical Chemists ("AOAC") 996.11 Starch (Total) in Cereal Products.

The method of the present disclosure may be combined with assays for starch, protein, fat, ash, moisture, or a combination thereof. The values of cellulose, hemicellulose, starch, protein, fat, ash, and moisture may be used to calculate the mass balance closure of the sample. Any suitable method for measuring the content of starch, protein, fat, ash, and moisture may be used. A method recognized for protein analysis is set forth in AOAC Official Method 990.03 Protein (Crude) In Animal Feed. One recognized method for fat analysis is set forth in AOAC Official Method 945.16 Oil in Cereal Adjuncts Petroleum Ether Extraction Method. A recognized method for ash analysis is set forth in AOAC Official Method 942.05 Ash of Animal Feed.

The result of the method may be an analysis result or analysis report obtained by the single-hydrolysis-step method as described herein. The analysis result or analysis report may state the hemicellulose content, cellulose content, cellulosic components content, or a combination thereof, of the sample, where the hemicellulose content, cellulose content, or cellulosic components content is obtained by the single-hydrolysis-step method as described herein. In some cases, the analysis result or analysis report states the hemicellulose content only. In some cases, the analysis result or analysis report states the cellulose content only. In some cases, the analysis result or analysis report states the hemicellulose content and the cellulose content. The hemicellulose content, cellulose content, or cellulosic components content may be calculated as described herein from the xylose, galactose, mannose, arabinose, and/or glucose content of the sample after hydrolysis.

EXPERIMENTAL

Various samples were tested using conventional analytical methods known in the art and the analytical methods described here.

Example 1

Various hydrolysis conditions were tested for hydrolyzing corn-based pre-conversion material and post-conversion samples. The hydrolysis conditions that were varied included incubation time and acid concentration. The samples were tested for hemicellulose and glucan content. The hydrolysis was performed at 85° C. for all of the samples. A pure corn starch sample was hydrolyzed at the same conditions to verify complete hydrolysis and recovery of the starch, as well as to confirm the absence of any substantial sugar degradation at the assay conditions.

The samples were prepared for analysis by drying, grinding, or both drying and grinding, as necessary, to achieve a moisture content of 10 wt-% or lower and a particle size to pass (at least 95 wt-%) through a 0.5 mm screen.

About 1.0 g±0.10 g of sample was weighed and mixed with 10 mL of various concentrations of sulfuric acid. The sample in the hydrolysis solution was incubated at 85° C. for varying amounts of time, mixing the sample every 60 min (if applicable). After incubation of the sample in the hydrolysis solution, a supernatant was separated from the suspension by centrifuging and filtering using a 25 μm filter. The supernatant was analyzed for glucose, xylose, mannose, galactose, and arabinose content using HPLC with an AMINEX HPX-87H column available from Bio-Rad Laboratories, Inc. in Hercules, CA. A blank and a starch standard were run alongside with the samples. The amount of hemicellulose in the sample was calculated using formula (I). The amount of total glucan was calculated using formula (II). The amount of cellulose was calculated according to formula (III).

The results are presented in FIGS. 1A-1F. It was observed that while pre-conversion material hemicellulose could effectively be hydrolyzed with 10 wt-% acid in about 2 hours, the hemicellulose of post-conversion material benefitted from a higher acid content and longer incubation times. Similarly, the glucan content of pre-conversion material could be quantified using as low as 20 wt-% acid concentration and an incubation period of about 2.5 hours, but to quantify glucan in post-conversion material, a higher acid content and incubation time were beneficial.

It was concluded that an acid concentration of 30 wt-% and incubation time of 60 min to 120 min at 85° C. could be used to substantially completely hydrolyze hemicellulose and total glucan in both types of samples. This substantially complete hydrolysis of both the hemicellulose and total glucan is demonstrated via the kinetic convergence of the hemicellulose and glucan totals for all samples when increasing both the acid concentration and the incubation time. As the values converge to a maximum over time and with increasing acid concentration, it was concluded that the reactions were taken to completion, thus giving assurance that all hemicellulose and glucan was converted to their respective monomeric saccharides. This is similar in fashion to a widely accepted scientific titration curve approach that ensures complete reaction of the target analytes by demonstrating a steadily increasing measured parameter until it reaches a consistent plateau or endpoint.

A starch standard was also utilized to further verify complete conversion of glucan as well as demonstrate that no substantial degradation of the sugars had occurred. The starch standard was analyzed with both increasing time and increasing acid concentration. Near complete recovery of the starch standard was achieved at all time intervals tested (ranging from 60 to 330 minutes). And when held at 330 minutes incubation time, near complete recovery of the starch standard was achieved with any acid concentration at or above 20% wt/wt.

Example 2

Various corn-based before conversion ("BC") and after conversion ("AC") samples were tested using the method of the present disclosure, and the results were compared to results achieved by conventional commercially available methods.

The samples were prepared for analysis by drying, grinding, or both drying and grinding, as necessary, to achieve a moisture content of 10 wt-% or lower and a particle size to pass (at least 95 wt-%) through a 0.5 mm screen.

About 1.0 g±0.10 g of sample was weighed and mixed with 10 mL of 30 wt-% sulfuric acid. The sample in the hydrolysis solution was incubated at 85° C. for 120 min, mixing the sample every 60 min. After incubation of the sample in the hydrolysis solution, a supernatant was separated from the suspension by centrifuging and filtering using a 0.2 μm filter. The supernatant was analyzed for glucose, xylose, mannose, galactose, and arabinose content as described in EXAMPLE 1.

The prepared samples were also analyzed using AOAC Official Method 990.03 for protein; AOAC Official Method 945.16 for fat; AOAC Official Method 942.05 for ash; and commercially available methods for NSSO (non-saccharide soluble organics) and starch (NSSO and starch results for biomass samples are available from Soliton, LLC in Sioux Falls, SD). The test results were used to calculate a cellulosic content by mass closure. The mass closure calculation relies on an assumption that everything that is not protein, fat, ash, starch, or NSSO, is cellulosic content (cellulose, hemicellulose, or lignin).

The amount of cellulose was also calculated from the total glucan and starch. Additionally, the amount of cellulosic components were calculated from the total glucan, starch, and hemicellulose. The converted % D3 RINs were calculated from the commercially available results for protein, fat, ash, NSSO, and starch (commercially available mass closure method), as well as from the calculated cellulose results using total glucan and starch and the cellulosic components using total glucan, starch, and hemicellulose. The results are shown in TABLES 1A-1C.

In TABLE 1A, cellulosic content by mass disclosure ("Cellulosic content MC") is calculated as:

100-% dw Protein-% dw Fat-% dw Ash-% dw Starch-% dw NSSO=% dw Cellulosic content. The results in TABLE 1A are given as % dry weight.

TABLE 1A

| | Commercially available method results. | | | | | |
|---|---|---|---|---|---|---|
| Sample ID | AOAC Protein | AOAC Fat | AOAC Ash | NSSO | Starch | Cellulosic content MC |
| 1BC | 9.37 | 5.03 | 1.93 | 1.34 | 70.19 | 12.15 |
| 1AC | 32.48 | 16.06 | 6.32 | 9.61 | 6.06 | 29.48 |
| 2BC | 9.49 | 4.83 | 1.76 | 1.85 | 69.59 | 12.48 |
| 2AC | 30.71 | 14.88 | 5.84 | 13.30 | 4.27 | 31.00 |
| 3BC | 9.31 | 4.98 | 1.99 | 1.96 | 69.50 | 12.26 |

TABLE 1A-continued

| | | | | | | |
|---|---|---|---|---|---|---|
| | | Commercially available method results. | | | | |
| Sample ID | AOAC Protein | AOAC Fat | AOAC Ash | NSSO | Starch | Cellulosic content MC |
| 3AC | 29.63 | 15.38 | 6.14 | 14.50 | 4.24 | 30.11 |
| 4BC | 9.45 | 5.25 | 1.82 | 1.89 | 69.70 | 11.88 |
| 4AC | 30.71 | 15.21 | 5.89 | 13.66 | 4.07 | 30.45 |
| 5BC | 9.63 | 4.97 | 1.99 | 2.53 | 67.65 | 13.24 |
| 5AC | 30.82 | 13.63 | 6.19 | 14.83 | 4.71 | 29.83 |
| 6BC | 8.94 | 5.16 | 1.95 | 0.82 | 69.61 | 13.52 |
| 6AC | 31.42 | 16.76 | 6.45 | 6.81 | 4.94 | 33.63 |
| 7BC | 9.82 | 6.17 | 2.34 | 1.09 | 67.88 | 12.71 |
| 7AC | 31.24 | 18.14 | 7.26 | 6.88 | 5.32 | 31.15 |
| 8BC | 9.11 | 5.17 | 1.93 | 1.86 | 70.27 | 11.67 |
| 8AC | 28.84 | 15.91 | 5.96 | 13.63 | 4.30 | 31.36 |
| 9BC | 8.96 | 5.09 | 1.92 | 1.87 | 70.40 | 11.75 |
| 9AC | 28.80 | 15.73 | 5.96 | 14.20 | 4.14 | 31.18 |
| 10BC | 9.04 | 5.13 | 1.94 | 1.86 | 70.30 | 11.74 |
| 10AC | 29.12 | 16.05 | 6.07 | 13.71 | 4.04 | 31.01 |
| 11BC | 9.81 | 5.21 | 1.81 | 1.80 | 69.43 | 11.94 |
| 11AC | 30.23 | 15.20 | 5.52 | 14.18 | 4.44 | 30.44 |
| 12BC | 10.20 | 5.44 | 1.86 | 2.03 | 68.78 | 11.70 |
| 12AC | 30.89 | 15.51 | 5.55 | 14.18 | 4.68 | 29.19 |
| 13BC | 9.11 | 5.17 | 1.93 | 1.86 | 70.27 | 11.67 |
| 13AC | 28.84 | 15.91 | 5.96 | 13.63 | 4.30 | 31.36 |
| 14BC | 8.96 | 5.09 | 1.92 | 1.87 | 70.40 | 11.75 |
| 14AC | 28.80 | 15.73 | 5.96 | 14.20 | 4.14 | 31.18 |
| 15BC | 9.04 | 5.13 | 1.94 | 1.86 | 70.30 | 11.74 |
| 15AC | 29.12 | 16.05 | 6.07 | 13.71 | 4.04 | 31.01 |
| 16BC | 9.52 | 2.90 | 1.78 | 0.77 | 71.62 | 13.41 |
| 16AC | 33.94 | 10.76 | 6.43 | 5.48 | 5.63 | 37.76 |
| 17BC | 9.37 | 2.84 | 1.80 | 0.74 | 72.07 | 13.18 |
| 17AC | 34.19 | 10.75 | 6.50 | 5.62 | 5.55 | 37.38 |

In TABLE 1B, cellulose is calculated by subtracting the starch content of TABLE 1A from the total glucan content ("Cellulose TG-Sta"). Cellulosic components are calculated by subtracting the starch content of TABLE 1A from the total glucan content and adding hemicellulose ("Cellulosic components TG-Sta+HC"). The results in TABLE 1B are given as % dry weight.

TABLE 1B

| | | | | |
|---|---|---|---|---|
| | | Present disclosure method results. | | |
| Sample ID | Hemicellulose | Total Glucan | Cellulose TG-Sta | Cellulosic components TG-Sta + HC |
| 1BC | 5.24 | 74.02 | 3.83 | 9.07 |
| 1AC | 16.67 | 9.08 | 3.02 | 19.70 |
| 2BC | 5.66 | 74.46 | 4.87 | 10.53 |
| 2AC | 17.15 | 8.52 | 4.25 | 21.40 |
| 3BC | 5.40 | 74.01 | 4.51 | 9.90 |
| 3AC | 16.20 | 8.32 | 4.08 | 20.28 |
| 4BC | 5.42 | 73.98 | 4.28 | 9.69 |
| 4AC | 16.55 | 7.99 | 3.92 | 20.47 |
| 5BC | 5.62 | 72.42 | 4.77 | 10.39 |
| 5AC | 16.80 | 8.45 | 3.74 | 20.54 |
| 6BC | 5.81 | 74.95 | 5.34 | 11.15 |
| 6AC | 18.31 | 8.75 | 3.81 | 22.12 |
| 7BC | 5.99 | 71.83 | 3.95 | 9.94 |
| 7AC | 17.72 | 8.29 | 2.97 | 20.69 |
| 8BC | 5.70 | 73.41 | 3.14 | 8.83 |
| 8AC | 17.89 | 8.09 | 3.79 | 21.68 |
| 9BC | 5.72 | 73.57 | 3.17 | 8.89 |
| 9AC | 17.69 | 8.20 | 4.06 | 21.75 |
| 10BC | 5.68 | 73.62 | 3.32 | 9.00 |
| 10AC | 17.92 | 7.88 | 3.84 | 21.76 |
| 11BC | 5.89 | 73.02 | 3.59 | 9.48 |
| 11AC | 17.75 | 8.16 | 3.72 | 21.47 |
| 12BC | 5.98 | 72.23 | 3.45 | 9.43 |
| 12AC | 17.37 | 8.68 | 4.00 | 21.37 |
| 13BC | 5.30 | 73.71 | 3.44 | 8.74 |
| 13AC | 17.08 | 8.65 | 4.35 | 21.43 |
| 14BC | 5.37 | 73.74 | 3.34 | 8.71 |

TABLE 1B-continued

| | | | | |
|---|---|---|---|---|
| | | Present disclosure method results. | | |
| Sample ID | Hemicellulose | Total Glucan | Cellulose TG-Sta | Cellulosic components TG-Sta + HC |
| 14AC | 17.53 | 7.87 | 3.73 | 21.26 |
| 15BC | 5.33 | 73.71 | 3.41 | 8.73 |
| 15AC | 17.46 | 7.90 | 3.86 | 21.32 |
| 16BC | 5.34 | 75.56 | 3.94 | 9.28 |
| 16AC | 19.19 | 9.73 | 4.10 | 23.29 |
| 17BC | 5.36 | 76.01 | 3.94 | 9.30 |
| 17AC | 19.28 | 9.86 | 4.31 | 23.59 |

In TABLE 1C. the % of gallons derived from the cellulosic content and cellulosic components ("% D3 RINs") are shown. The % D3 RINs are calculated from the mass closure, glucan, hemicellulose, and cellulose results above, using EPA prescribed calculations.

TABLE 1C

| | | | |
|---|---|---|---|
| | | % D3 RINs results. | |
| Sample ID | % D3 RINs from Cellulosic content MC | % D3 RINs from Cellulose TG-Sta | % D3 RINs from Cellulosic components TG-Sta + HC |
| 1BC | 4.40% | 4.07% | 4.28% |
| 1AC | | | |
| 2BC | 4.39% | 4.99% | 5.64% |
| 2AC | | | |
| 3BC | 3.54% | 4.46% | 4.66% |
| 3AC | | | |
| 4BC | 3.48% | 4.29% | 4.69% |
| 4AC | | | |
| 5BC | 5.23% | 5.12% | 5.42% |
| 5AC | | | |
| 6BC | 4.69% | 5.79% | 6.15% |
| 6AC | | | |
| 7BC | 3.88% | 4.32% | 4.71% |
| 7AC | | | |
| 8BC | 2.15% | 2.70% | 2.57% |
| 8AC | | | |
| 9BC | 2.41% | 2.62% | 2.66% |
| 9AC | | | |
| 10BC | 2.58% | 2.94% | 2.88% |
| 10AC | | | |
| 11BC | 2.80% | 3.37% | 3.46% |
| 11AC | | | |
| 12BC | 2.77% | 3.05% | 3.27% |
| 12AC | | | |
| 13BC | 2.15% | 2.87% | 2.55% |
| 13AC | | | |
| 14BC | 2.41% | 3.01% | 2.63% |
| 14AC | | | |
| 15BC | 2.58% | 3.06% | 2.71% |
| 15AC | | | |
| 16BC | 4.05% | 3.84% | 3.88% |
| 16AC | | | |
| 17BC | 3.86% | 3.75% | 3.78% |
| 17AC | | | |

Figure 2A:
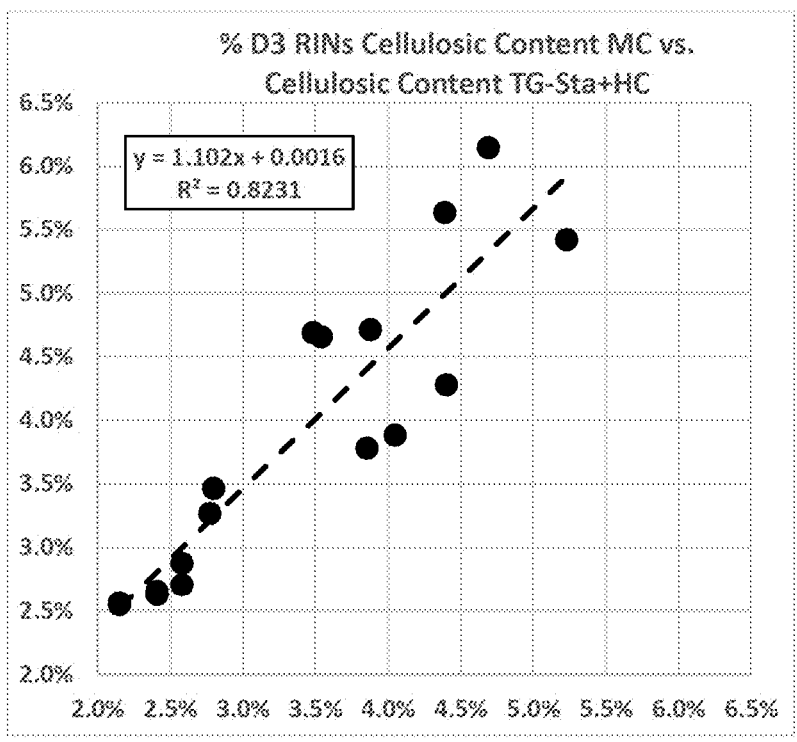
FIGS. 2A and 2B are graphical representations of data from EXAMPLE 2.
Figure 2B:
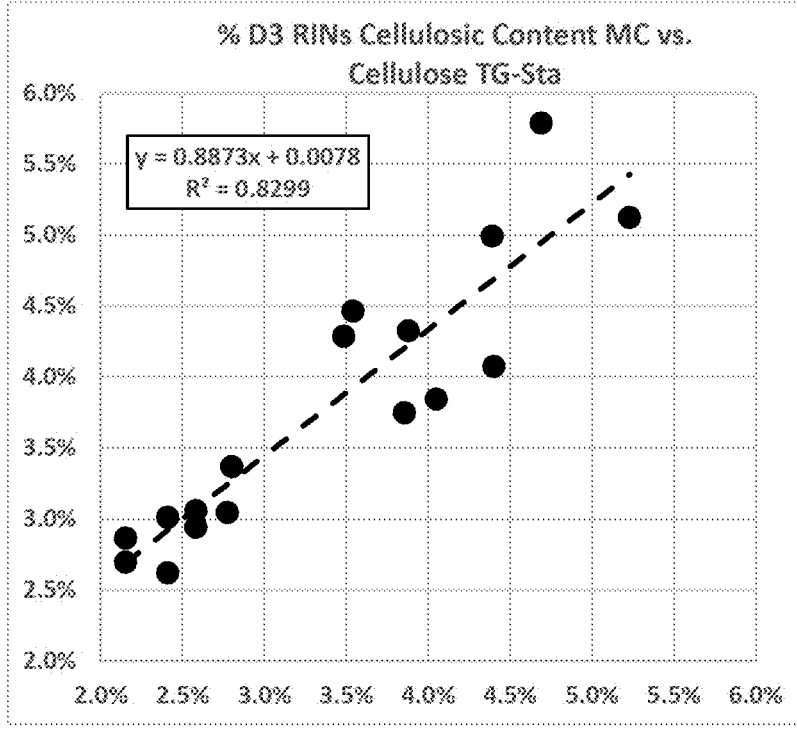

The correlation of % D3 RINs calculated from cellulosic content MC and the % D3 RINS calculated from cellulosic components TG-Sta+HC according to the present disclosure is plotted in a graph shown in FIG. 2A. The correlation of % D3 RINs calculated from cellulosic content MC and the % D3 RINs calculated from cellulose TG-Sta according to the present disclosure is plotted in a graph shown in FIG. 2B.

It was observed that the results from the % D3 RINs calculated from cellulosic components (total glucan minus starch plus hemicellulose; TG-Sta+HC) results according to the present disclosure correlate well with the % D3 RINs calculated from the commercially available cellulosic content based on mass closure results (cellulosic content MC), exhibiting a coefficient of correlation ($R^2$) of 82%.

It was observed that the results from the % D3 RINs calculated from cellulose only (total glucan minus starch; TG-Sta) according to the present disclosure also correlate well with the % D3 RINs calculated from the commercially available cellulosic content based on mass closure results (cellulosic content MC), exhibiting a coefficient of correlation ($R^2$) of 83%.

It was concluded that the analytical test results obtained—using the method of the present disclosure for both cellulosic components (total glucan minus starch plus hemicellulose; TG-Sta+HC) and cellulose only (total glucan minus starch; TG-Sta)—correlated well with the commercially available cellulosic content based on mass closure results (cellulosic content MC). Additionally, given that the method of present disclosure can speciate the cellulosic components, it was concluded that the user of this method would have the ability to determine the converted fractions separately between cellulose and hemicellulose in addition to total cellulosic content. This is of great utility when trying to determine the efficacy of cellulase and hemicellulase enzyme treatments and the efficacy of the various microorganisms used in fermentation to convert both pentose and hexose monosaccharides to ethanol. Furthermore, using the method of present disclosure the user would have the ability to calculate the percentage of cellulosic ethanol (% D3 RINs) derived from cellulose and hemicellulose separately.

Example 3

Two biomass test materials (18BC and 18AC) were analyzed using the method of the present disclosure (e.g., as in EXAMPLE 2) and a student laboratory experiment test method for fiber, where students were instructed to hydrolyze samples at room temperature and at 90° C.

Sample 18BC was a before conversion material sample having a high starch content, exemplified by the high total glucan result. Sample 18AC was an after conversion material sample having a low starch content and relatively high hemicellulose content.

The student laboratory experiment was performed according to University of Maryland Department of Chemical & Biomolecular Engineering course ENCH485 Experiment No. 4, Cellulose Degradation. Sample suspensions of Sample 18BC and Sample 18AC were prepared by mixing an amount of sample with aqueous sulfuric acid having a concentration of 5 wt-%. Sample suspensions were then incubated at 25° C. (room temperature, "RT") and at 90° C. for 120 min. Following incubation, sample supernatant was separated from the suspension and analyzed for glucose, xylose, mannose, galactose, and arabinose content.

Results are shown in TABLE 2 below. All results are given as % dry weight.

TABLE 2

Comparative test results.

| Test Parameter | | Sample 18BC | Sample 18AC |
|---|---|---|---|
| Present disclosure | Total glucan, wt-% | 76.4 | 7.2 |
| | Hemicellulose, wt-% | 5.5 | 18.0 |
| | Cellulose, wt-% | 5.5 | 3.2 |
| | Cellulosic components, wt-% | 11.0 | 21.2 |
| Student laboratory | RT total glucan, wt-% | 1.7 | 0.5 |
| | RT hemicellulose, wt-% | 1.0 | 0.9 |

TABLE 2-continued

Comparative test results.

| Test Parameter | | Sample 18BC | Sample 18AC |
|---|---|---|---|
| method | 90° C. total glucan, wt-% | 43.0 | 2.6 |
| | 90° C. hemicellulose, wt-% | 4.7 | 13.9 |

It was observed that the student method gave lower values for both total glucan and hemicellulose of both samples and at both test conditions (room temperature and at 90° C.). The room temperature test was further away than the high temperature test from the results obtained by the method of the present disclosure, but even the high temperature test failed to reach more than 56.3% recovery of the total glucan and 84.9% recovery of the hemicellulose.

It was concluded that the method of present disclosure had significantly higher recovery of both cellulose and hemicellulose for all samples when compared to the University of Maryland methods.

Example 4

Various samples of #2 Yellow Corn were tested using the method of the present disclosure, and the results were compared to results achieved by conventional commercially available methods.

The samples were prepared for analysis by drying, grinding, or both drying and grinding, as necessary, to achieve a moisture content of 10 wt-% or lower and a particle size to pass (at least 95 wt-%) through a 0.5 mm screen.

About 1.0 g±0.10 g of sample was weighed and mixed with 10 mL of 30 wt-% sulfuric acid. The sample in the hydrolysis solution was incubated at 85° C. for 120 min, mixing the sample every 60 min. After incubation of the sample in the hydrolysis solution, a supernatant was separated from the suspension by centrifuging and filtering using a 0.2 μm filter. The supernatant was analyzed for glucose, xylose, mannose, galactose, and arabinose content as described in EXAMPLE 1.

In TABLE 3, cellulosic content by mass disclosure ("Cellulosic content MC") is calculated as:

$$100 - \% \, dw \, \text{Protein} - \% \, dw \, \text{Fat} - \% \, dw \, \text{Ash} -$$
$$\% \, dw \, \text{Starch} - \% \, dwNSSO = \% \, dw \, \text{Cellulosic content}.$$

And in TABLE 3, cellulose is calculated by subtracting the starch content from the total glucan content ("Cellulose TG-Sta"). Cellulosic components using the present disclosure method ("Cellulosic components TG-Sta+HC") is calculated by subtracting the starch content of from the total glucan content and adding hemicellulose. The results in TABLE 3 are given as % dry weight.

Figure 3A:
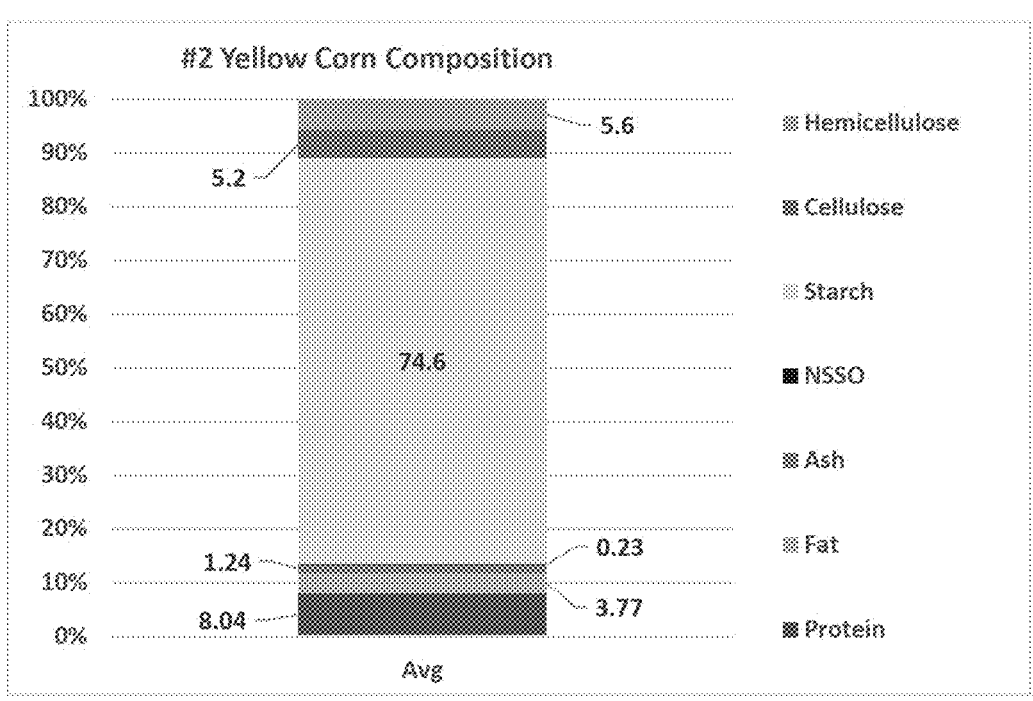
FIGS. 3A and 3B are graphical representations of data from EXAMPLE 4.

FIG. 3A shows average mass closure of all the #2 Yellow Corn samples. The average mass closure was 98.7%.

Figure 3B:
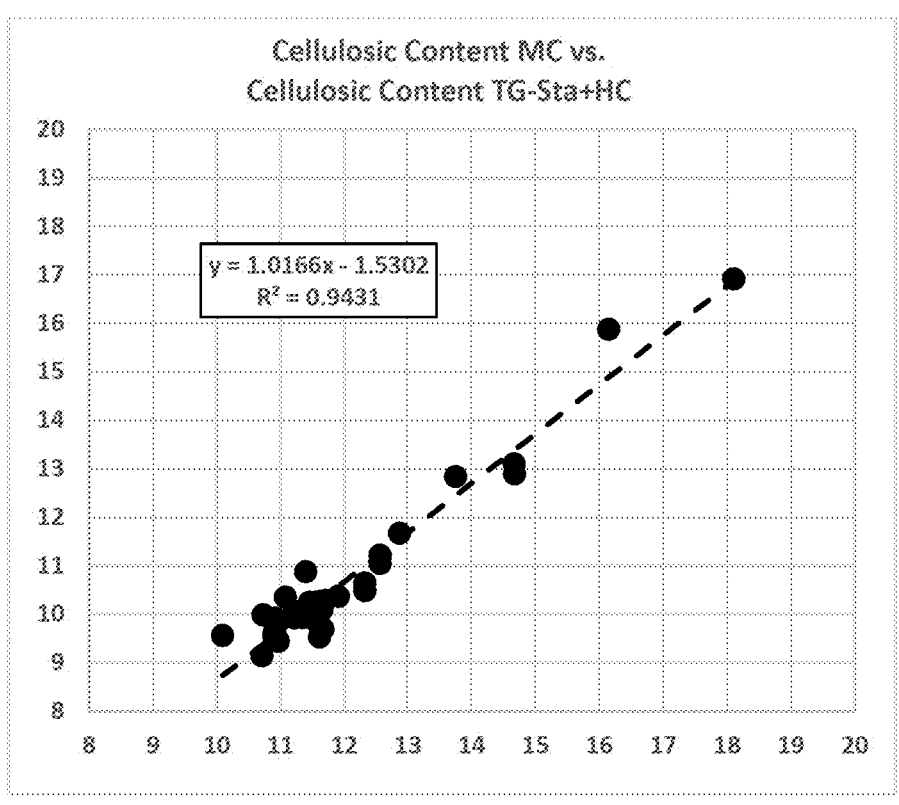

FIG. 3B shows the correlation between the cellulosic content as measured by the commercially available mass closure method and the method of present disclosure. The cellulosic components as measured by the method of present disclosure correlated well with cellulosic content as measured by the commercially available mass closure method, exhibiting a coefficient of correlation ($R^2$) of 94%.

TABLE 3

| | Commercially Available Method Results | | | | | | Method of Present Disclosure Results | | | | |
| --- | --- | --- | --- | --- | --- | --- | --- | --- | --- | --- | --- |
| Sample ID | AOAC Protein % dw | AOAC Fat % dw | AOAC Ash % dw | NSSO % dw | Starch % dw | Cellulosic content MC % dw | Total Glucan % dw | Hemicellulose % dw | Cellulose TG-Sta % dw | Cellulosic components TG-Sta + HC % dw | Mass Closure |
| Sample #1 | 8.1 | 3.8 | 1.2 | 0.2 | 75.1 | 11.6 | 79.3 | 5.4 | 4.1 | 9.5 | 97.9 |
| Sample #2 | 7.7 | 3.7 | 1.2 | 0.2 | 75.9 | 11.4 | 80.2 | 5.5 | 4.4 | 9.9 | 98.6 |
| Sample #3 | 7.6 | 3.8 | 1.3 | 0.2 | 71.0 | 16.2 | 81.5 | 5.4 | 10.5 | 15.9 | 99.7 |
| Sample #4 | 7.6 | 3.9 | 1.2 | 0.2 | 76.1 | 10.9 | 80.4 | 5.6 | 4.3 | 9.9 | 99.0 |
| Sample #5 | 9.3 | 3.9 | 1.3 | 0.3 | 70.5 | 14.7 | 77.9 | 5.7 | 7.4 | 13.1 | 98.4 |
| Sample #6 | 7.4 | 3.9 | 1.1 | 0.2 | 76.5 | 10.9 | 80.6 | 5.5 | 4.1 | 9.6 | 98.7 |
| Sample #7 | 8.2 | 3.6 | 1.3 | 0.3 | 74.9 | 11.7 | 79.6 | 5.5 | 4.8 | 10.3 | 98.6 |
| Sample #8 | 8.3 | 3.8 | 1.3 | 0.2 | 73.9 | 12.6 | 79.1 | 5.9 | 5.2 | 11.0 | 98.5 |
| Sample #9 | 8.3 | 3.8 | 1.3 | 0.4 | 73.9 | 12.3 | 78.6 | 5.8 | 4.7 | 10.5 | 98.2 |
| Sample #10 | 7.6 | 3.6 | 1.2 | 0.2 | 75.9 | 11.6 | 80.2 | 5.6 | 4.3 | 9.9 | 98.3 |
| Sample #11 | 7.6 | 3.6 | 1.1 | 0.2 | 75.9 | 11.6 | 80.6 | 5.6 | 4.7 | 10.3 | 98.7 |
| Sample #12 | 8.1 | 3.8 | 1.2 | 0.3 | 75.6 | 11.1 | 80.5 | 5.4 | 4.9 | 10.3 | 99.3 |
| Sample #13 | 7.8 | 3.7 | 1.2 | 0.2 | 75.5 | 11.7 | 79.9 | 5.8 | 4.4 | 10.2 | 98.5 |
| Sample #14 | 7.9 | 3.7 | 1.1 | 0.2 | 73.3 | 13.8 | 80.7 | 5.5 | 7.3 | 12.8 | 99.1 |
| Sample #15 | 8.5 | 3.8 | 1.3 | 0.1 | 74.8 | 11.5 | 79.1 | 6.0 | 4.3 | 10.2 | 98.8 |
| Sample #16 | 7.9 | 3.7 | 1.3 | 0.2 | 74.1 | 12.9 | 80.1 | 5.6 | 6.0 | 11.7 | 98.8 |
| Sample #17 | 7.8 | 3.8 | 1.2 | 0.2 | 75.5 | 11.7 | 79.9 | 5.7 | 4.4 | 10.1 | 98.4 |
| Sample #18 | 7.8 | 3.7 | 1.2 | 0.2 | 75.8 | 11.2 | 80.1 | 5.7 | 4.3 | 9.9 | 98.7 |
| Sample #19 | 10.2 | 3.7 | 1.4 | 0.2 | 66.5 | 18.1 | 78.8 | 4.6 | 12.3 | 16.9 | 98.8 |
| Sample #20 | 7.5 | 3.7 | 1.2 | 0.2 | 75.7 | 11.7 | 79.8 | 5.6 | 4.1 | 9.7 | 98.0 |
| Sample #21 | 7.8 | 3.8 | 1.3 | 0.3 | 75.9 | 11.0 | 79.7 | 5.6 | 3.8 | 9.4 | 98.5 |
| Sample #22 | 8.1 | 3.8 | 1.2 | 0.2 | 76.7 | 10.1 | 80.7 | 5.6 | 4.0 | 9.6 | 99.5 |
| Sample #23 | 7.9 | 4.0 | 1.3 | 0.2 | 75.2 | 11.4 | 80.4 | 5.7 | 5.2 | 10.9 | 99.5 |
| Sample #24 | 8.2 | 4.0 | 1.3 | 0.2 | 74.5 | 11.9 | 79.0 | 5.8 | 4.5 | 10.4 | 98.5 |
| Sample #25 | 7.7 | 3.9 | 1.2 | 0.3 | 75.7 | 11.2 | 80.2 | 5.6 | 4.4 | 10.1 | 98.8 |
| Sample #26 | 7.7 | 3.9 | 1.3 | 0.2 | 76.2 | 10.7 | 80.7 | 5.5 | 4.5 | 10.0 | 99.3 |
| Sample #27 | 7.6 | 3.6 | 1.2 | 0.2 | 75.9 | 11.6 | 80.1 | 5.6 | 4.2 | 9.9 | 98.3 |
| Sample #28 | 7.6 | 3.9 | 1.2 | 0.2 | 76.1 | 10.9 | 80.2 | 5.6 | 4.1 | 9.7 | 98.7 |
| Sample #29 | 9.3 | 3.9 | 1.3 | 0.3 | 70.5 | 14.7 | 77.6 | 5.8 | 7.1 | 12.9 | 98.2 |
| Sample #30 | 7.4 | 3.9 | 1.1 | 0.2 | 76.5 | 10.9 | 80.5 | 5.6 | 4.0 | 9.5 | 98.6 |
| Sample #31 | 8.2 | 3.6 | 1.3 | 0.3 | 75.9 | 10.7 | 79.5 | 5.5 | 3.6 | 9.1 | 98.4 |
| Sample #32 | 8.3 | 3.8 | 1.3 | 0.2 | 73.9 | 12.6 | 79.1 | 6.0 | 5.3 | 11.2 | 98.7 |
| Sample #33 | 8.3 | 3.8 | 1.3 | 0.4 | 73.9 | 12.3 | 78.7 | 5.8 | 4.8 | 10.6 | 98.3 |
| Min: | 7.4 | 3.6 | 1.1 | 0.1 | 66.5 | 10.1 | 77.6 | 4.6 | 3.6 | 9.1 | 97.9 |
| Max: | 10.2 | 4.0 | 1.4 | 0.4 | 76.7 | 18.1 | 81.5 | 6.0 | 12.3 | 16.9 | 99.7 |
| Average | 8.0 | 3.8 | 1.2 | 0.2 | 74.6 | 12.1 | 79.8 | 5.6 | 5.2 | 10.8 | 98.7 |

It was concluded that the cellulosic components as measured by the method of present disclosure correlated well with cellulosic content as measured by the commercially available mass closure method. Furthermore, when the cellulose and hemicellulose results from the method of present disclosure are added to the other compositional analysis components of protein, fat, ash, starch, and NSSO, the mass closure is essentially complete (because corn-based products include very little, if any, lignin), exhibiting an average mass closure of 98.7%. This complete mass closure adds to the confirmation that the method of present disclosure is completely and accurately accessing the hemicellulose and cellulose fractions. This is in addition to the kinetic convergence confirmation conclusion found in EXAMPLE 1.

All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. It should be understood that this disclosure is not intended to be unduly limited by the illustrative embodiments and examples set forth herein and that such examples and embodiments are presented by way of example only with the scope of the disclosure intended to be limited only by the claims set forth here.

The invention claimed is:

1. A method for quantifying a cellulosic component in a sample, the method comprising:

preparing a suspension by mixing an amount of the sample with aqueous sulfuric acid having a concentration of 15 wt-% to 60 wt-%;

incubating the suspension and hydrolyzing the cellulosic component at an incubation temperature of 50° C. to 98° C. at ambient pressure for an incubation period of 30 min to 360 min, wherein the sample is not subjected to hydrolysis at temperatures above 98° C.;

separating a supernatant from the suspension;

analyzing the supernatant for total content of xylose, mannose, galactose, and arabinose;

preparing and analyzing a blank sample alongside with the sample; and calculating, based on the analysis, an amount of the cellulosic component, wherein the cellulosic component comprises hemicellulose, and wherein calculating the amount of hemicellulose comprises:

$$\% \ dw \ \text{Total Hemicellulose} = ((((X-Y+S-T)/100)*(A+R))/A)/(1.136*(D/100))*100, \text{ where:}$$

R is a total weight of liquid added to the sample;

A is mass of the sample;

D is wt-% total solids content of the sample;

S is the arabinose content of the supernatant in wt-%;

T is an HPLC result representative of arabinose of the blank sample in wt-%;

X is a combined xylose, galactose, and mannose content of the supernatant in wt-%; and Y is an HPLC result representative of combined xylose, galactose, and mannose of the blank sample in wt-%.

2. The method of claim 1, wherein the sample is corn-based.

3. The method of claim 1, wherein the sample comprises raw ground corn.

4. The method of claim 1, wherein the sample comprises a starting material, an intermediate product, or a final product from a corn-to-ethanol production process.

5. The method of claim 1, wherein the amount of sample is mixed with an amount of the aqueous sulfuric acid that is from 8 to 12 parts of aqueous sulfuric acid to every 1 part sample.

6. The method of claim 1, wherein the sample is not subjected to hydrolysis at temperatures above 90° C.

7. The method of claim 1, wherein the sample is only subjected to temperatures of 90° C. or lower during the method.

8. The method of claim 1, wherein the acid concentration is from 15 wt-% to 45 wt-%.

9. The method of claim 1, wherein the supernatant is substantially free of furfural and hydroxymethylfurfural.

10. The method of claim 1, wherein the method does not include enzymatic hydrolysis.

11. The method of claim 1, wherein the method causes hydrolysis of the sample, and wherein hydrolysis consists of the incubating of the suspension at the incubation temperature for the incubation period.

12. The method of claim 1, wherein the incubation period is 60 min to 150 min.

13. The method of claim 1 comprising determining an amount of ethanol produced from cellulosic content as % D3 RIN.

14. A method for quantifying a cellulosic component in a sample, the method comprising:

hydrolyzing the sample, the hydrolyzing consisting of a single acid hydrolysis of the sample in aqueous sulfuric acid having a concentration of 15 wt-% to 60 wt-%, at an incubation temperature of 50° C. to 98° C., at ambient pressure, for an incubation period of 30 min to 360 min;

separating a supernatant from the hydrolyzed sample in aqueous sulfuric acid;

analyzing the supernatant for total content of xylose, mannose, galactose, and arabinose;

preparing and analyzing a blank sample alongside with the sample; and calculating, based on the analysis, an amount of the cellulosic component, wherein the cellulosic component comprises hemicellulose, and wherein calculating the amount of hemicellulose comprises:

$$\% \, dw \, \text{Total Hemicellulose}=((((X{-}Y{+}S{-}T)/100){*}(A{+}R))/A)/(1.136{*}(D/100)){*}100, \text{ where:}$$

R is a total weight of liquid added to the sample;

A is mass of the sample;

D is wt-% total solids content of the sample;

S is the arabinose content of the supernatant in wt-%;

T is an HPLC result representative of arabinose of the blank sample in wt-%;

X is a combined xylose, galactose, and mannose content of the supernatant in wt-%; and Y is an HPLC result representative of combined xylose, galactose, and mannose of the blank sample in wt-%.

15. The method of claim 14, wherein the sample is corn-based.

16. The method of claim 14, wherein the sample comprises a starting material, an intermediate product, or a final product from a corn-to-ethanol production process.

17. The method of claim 14, wherein the sample is not subjected to hydrolysis at temperatures above 90° C.

18. The method of claim 14, wherein the supernatant is substantially free of furfural and hydroxymethylfurfural.

19. The method of claim 14, wherein the method does not include enzymatic hydrolysis.

\* \* \* \* \*